United States Patent [19]

LeMahieu

[11] 4,282,360

[45] * Aug. 4, 1981

[54] 7-METHYLTHIO OR METHYLSULFINYL-5-OXO-5H-THIAZOLO[2,3-B]QUINAZOLINE-2-CARBOXYLIC ACID

[75] Inventor: Ronald A. LeMahieu, North Caldwell, N.J.

[73] Assignee: Hoffmann-La Roche Inc., Nutley, N.J.

[*] Notice: The portion of the term of this patent subsequent to Sep. 18, 1996, has been disclaimed.

[21] Appl. No.: 84,471

[22] Filed: Oct. 12, 1979

[51] Int. Cl.³ ............... C07D 513/14; C07D 239/72; C07D 495/04
[52] U.S. Cl. ............................ 544/250; 424/251
[58] Field of Search .................. 544/250; 424/251

[56] References Cited

U.S. PATENT DOCUMENTS

| | | | |
|---|---|---|---|
| 4,041,163 | 8/1977 | Bindra et al. | 424/251 |
| 4,083,980 | 4/1978 | Schromm et al. | 424/251 |
| 4,122,274 | 10/1978 | Juby | 544/282 |
| 4,168,380 | 9/1979 | LeMahieu | 544/250 |

*Primary Examiner*—Donald G. Daus
*Assistant Examiner*—Diana G. Rivers
*Attorney, Agent, or Firm*—Jon S. Saxe; Bernard S. Leon; William G. Isgro

[57] ABSTRACT

7-Methylthio or methylsulfinyl-5-oxo-5H-thiazolo[2,3-b]quinazoline-2-carboxylic acid, useful as antiallergic agents, and prepared by the reaction of 5-methylthioanthranilic acid with methyl 2-chlorothiazole-5-carboxylate, subsequent hydrolysis, and, as necessary, oxidation to the corresponding sulfoxide, is described.

3 Claims, No Drawings

7-METHYLTHIO OR METHYLSULFINYL-5-OXO-5H-THIAZOLO[2,3-B]QUINAZOLINE-2-CARBOXYLIC ACID

BRIEF SUMMARY OF THE INVENTION

The invention relates to 7-methylthio or methylsulfinyl-5-oxo-5H-thiazolo[2,3-b]quinazoline-2-carboxylic acid, characterized by the structure

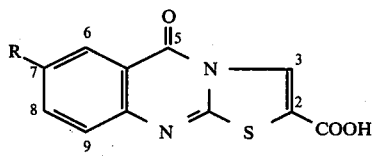

wherein R is methylthio or methylsulfinyl, and salts thereof with pharmaceutically acceptable bases. The compounds of formula I are useful as antiallergic agents.

DETAILED DESCRIPTION OF THE INVENTION

The compounds of the invention, that is, 7-methylthio or methylsulfinyl-5-oxo-5H-thiazolo[2,3-b]quinazoline-2-carboxylic acid, characterized by the formula

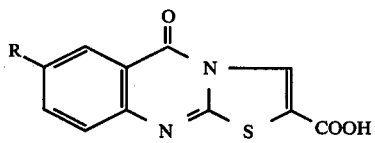

wherein R is methylthio or methylsulfinyl, can be prepared by condensing 5-methylthioanthranilic acid or the corresponding methyl ester with a 2-halothiazole of the formula

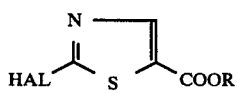

wherein R is hydrogen or lower alkyl. When R is hydrogen, the 7-methylthio-5-oxo-5H-thiazolo[2,3-b]quinazoline-2-carboxylic acid is recovered. When R is lower alkyl, an ester of the formula

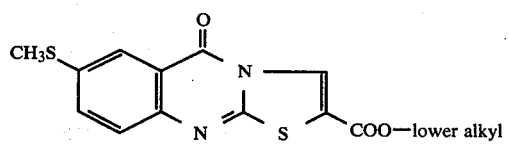

is formed and is sequentially treated with a base and an acid to yield the desired 7-methylthio-5-oxo-5H-thiazolo[2,3-b]quinazoline-2-carboxylic acid. The 7-methylsulfinyl-5-oxo-5H-thiazolo[2,3-b]quinazoline-2-carboxylic acid is prepared by oxidation of the 7-methylthio-5-oxo-5H-thiazolo[2,3-b]quinazoline-2-carboxylic acid.

As used herein, the term "lower alkyl" denotes an alkyl radical of 1–7 carbon atoms, such as methyl, ethyl, propyl, butyl, and the like.

The condensation of 5-methylthioanthranilic acid or the corresponding methyl ester with the compound of formula II is carried out, preferably, at a temperature in the range of from about 150° to about 180° C. The condensation is usually carried out without added solvent. However, a high boiling polar solvent such as triglyme, dimethylformamide, or the like can be utilized. Furthermore, the condensation can be carried out with or without a catalyst. Exemplary of such catalysts are, for example, alkali metal iodides, such as sodium iodide, lithium iodide; preferably potassium iodide. The condensation can also be carried out in a solvent such as 2-methoxyethanol at 124° with a catalytic amount of formic acid.

The conversion of the ester of formula III to the desired acid, can be carried out in an excess of alkali metal hydroxide, for example, sodium hydroxide, potassium hydroxide, or the like, at a temperature preferably in the range of from about 0° to about 30° C. Most preferably, the reaction is carried out at about 25° C. The hydrolysis is followed by refluxing with an organic carboxylic acid such as acetic acid, propionic acid, or the like. The desired 7-methoxy-5-oxo-5H-thiazolo[2,3-b]quinazoline-2-carboxylic acid can be recovered, in the process referred to above, utilizing conventional procedures such as recrystallization, or the like.

The 7-methylthio-5-oxo-5H-thiazolo[2,3-b]quinazoline-2-carboxylic acid is converted to the 7-methylsulfinyl-5-oxo-5H-thiazolo[2,3-b]quinazoline-2-carboxylic acid by an oxidation which is carried out utilizing an oxidizing agent, for example, sodium periodate or the like. The temperature of the oxidation is not critical and can normally comprise room temperature.

The compounds of formula I form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium ethanolate, potassium ethanolate, and the like; organic bases such as piperidine, diethylamine, N-methylglucamine, and the like.

The compounds of formula I, that is, 7-methylthio-5-oxo-5H-thiazolo[2,3-b]-quinazoline-2-carboxylic acid, 7-methylsulfinyl-5-oxo-5H-thiazolo[2,3-b]quinazoline-2-carboxylic acid, and their pharmaceutically acceptable salts inhibit cutaneous anaphylaxis in rats, and are therefore useful in the prevention of allergic reactions, for example, they are useful in the prophylactic treatment of bronchial asthma. The anti-anaphylactic activity can be demonstrated by the passive cutaneous anaphylaxis assay (PCA Test) in the rat. This test involves passive local sensitization of rats by intradermal injection of anti-sera. After a latent period of 24 hours, the test compound, in this case, 7-methylthio-5-oxo-5H-thiazolo[2,3-b]quinazoline-2-carboxylic acid or 7-methylsulfinyl-5-oxo-5H-thiazolo[2,3-b]quinazoline-2-carboxylic acid is given intraperitoneally followed after 5 minutes by an intravenous injection of reagin and Evans blue dye. The events associated with localized antigen-antibody reaction lead to the formation of skin wheals whose sizes are measured. The ability of the test compound to decrease the size of the wheals compared to controls is taken as a measure of its activity.

When 7-methylthio-5-oxo-5H-thiazolo[2,3-b]quinazoline-2-carboxylic acid, which has an $LD_{50}$ intraperitoneally of 450 mg/kg, is utilized as the test compound at a dose of 16 mg/kg. intraperitoneally, the reduction in the wheal size is 80%.

When 7-methylsulfinyl-5-oxo-5H-thiazolo[2,3-b]quinazoline-2-carboxylic acid is utilized as the test compound at a dose of 16 mg/kg. intraperitoneally, the reduction in the wheal size is 50%.

When 7-methylthio-5-oxo-5H-thiazolo[2,3-b]quinazoline-2-carboxylic acid, which has an $LD_{50}$ of >1000 mg/kg, is utilized as the test compound at a dose of 32 mg/kg. orally, the reduction in the wheal size is 87%. The compound has an $ID_{50}$ of 0.12 mg/kg, orally.

When 7-methylsulfinyl-5-oxo-5H-thiazolo[2,3-b]quinazoline-2-carboxylic acid is utilized as the test compound at a dose of 32 mg/kg. orally, the reduction in the wheal size is 67%. The compound has an $ID_{50}$ of 1.82 mg/kg, orally.

The 7-methylthio-5-oxo-5H-thiazolo[2,3-b]quinazoline-2-carboxylic acid, and 7-methylsulfinyl-5-oxo-5H-thiazolo[2,3-b]quinazoline-2-carboxylic acid, or their pharmaceutically acceptable salts can be administered orally or parenterally as antiallergic agents, for example, in the prophylactic treatment of bronchial asthma, with dosage adjustments for individual requirements. They can be administered therapeutically, for example, orally or parenterally, by incorporating a therapeutic dosage in a conventional dosage form, such as tablets, capsules, elixirs, suspensions, solutions, aerosols or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity, and the pharmaceutical dosage forms can, if desired, be subjected to conventional pharmaceutical expedients such as, for example, sterilization. As stated above, the dosage can be adjusted to individual requirements. They can also contain other therapeutically valuable substances.

The quantity of active medicament which is present in any of the abovedescribed dosage forms is variable. It is preferred, however, to provide capsules or tablets containing from about 10 mg. to about 20 mg. of 7-methylthio-5-oxo-5H-thiazolo[2,3-b]quinazoline-2-carboxylic acid, or 7-methylsulfinyl-5-oxo-5H-thiazolo[2,3-b]quinazoline-2-carboxylic acid, or an equivalent amount of a medicinally acceptable acid addition salt thereof.

The frequency with which any such dosage form will be administered to a warm-blooded mammal will vary, depending upon the quantity of active medicament present therein and the needs and requirements of the warm-blooded mammal. Under ordinary circumstances, however, up to about 20 mg/kg. of 7-methylthio-5-oxo-5H-thiazolo[2,3-b]quinazoline-2-carboxylic acid or 7-methylsulfinyl-5-oxo-5H-thiazolo[2,3-b]quinazoline-2-carboxylic acid can be administered daily in several dosages. It is to be understood, however, that the dosages set forth therein are exemplary only and that they do not, to any extent, limit the scope or practice of this invention.

As used herein, the term "HAL" denotes a halogen, such as, chlorine, bromine, fluorine or iodine.

The Examples which follow further illustrate the invention. All temperatures are given in degrees Centigrade, unless otherwise mentioned.

EXAMPLE 1

Preparation of 7-(methylthio)-5-oxo-5H-thiazolo[2,3-b]quinazoline-2-carboxylic acid An intimate mixture of 4.45 g. of methyl 5-methylthioanthranilate, 4.00 g. of methyl 2-chlorothiazole-5-carboxylate and 0.23 g. of potassium iodide was stirred and heated in an oil bath at 160° for 40 minutes. The resultant solid was treated with 50 ml. of saturated sodium bicarbonate and extracted with chloroform. The dried magnesium sulfate extract was concentrated in vacuo to a solid which was triturated with 100 ml. of ether and filtered to give 5.1 g. of methyl 7-(methylthio)-5-oxo-5H-thiazolo[2,3-b]quinazoline-2-carboxylate, mp 195°-197°. The ester obtained was hydrolyzed by stirring at room temperature with 160 ml. of 1 N sodium hydroxide and 200 ml. of methanol for 16 hours. After acidification with acetic acid, most of the solvent was removed in vacuo. Water was added. The resultant solid was removed by filtration, and it was refluxed in acetic acid for 1 hour and the solution was then allowed to cool. The crystalline solid was filtered to give 3.57 g. of pure 7-(methylthio)-5-oxo-5H-thiazolo-[2,3-b]quinazoline-2-carboxylic acid, mp 253°-255°.

EXAMPLE 2

Preparation of 7-(methylsulfinyl)-5-oxo-5H-thiazolo[2,3-b]quinazoline-2-carboxylic acid To 1.022 g. of 7-(methylthio)-5-oxo-5H-thiazolo[2,3-b]quinazoline-2-carboxylic acid suspended in 25 ml. of water cooled in an ice bath was added 3.5 ml. of 1.0 N sodium hydroxide. After a few minutes, 0.824 g. of sodium periodate was added. The solution was stirred in the ice bath for 2 hours and at room temperature for 4 hours. After the addition of 3.8 ml. of 1.0 N hydrochloric acid, the resultant solid was removed by filtration and recrystallized from acetic acid to yield 0.829 g. of pure 7-(methylsulfinyl)-5-oxo-5H-thiazolo[2,3-b]quinazoline-2-carboxylic acid, mp 243°-244°.

EXAMPLE 3

Capsule Formulation

|  | mg/capsule | |
| --- | --- | --- |
|  | 10 mg. | 20 mg |
| 7-Methylthio-5-oxo-5H-thiazolo-[2,3-b]quinazoline-2-carboxylic acid | 10.0 | 20.0 |
| Lactose | 215.0 | 205.0 |
| Cornstarch | 60.0 | 60.0 |
| Magnesium Stearate | 3.0 | 3.0 |
| Talc | 12.0 | 12.0 |
| Total | 300 mg. | 300 mg. |

Procedure:

Mix 7-methylthio-5-oxo-5H-thiazolo[2,3-b]quinazoline-2-carboxylic acid, lactose and cornstarch in a suitable mixer. Mill through suitable mill. Mix with magnesium stearate and talc and fill on capsule machine.

EXAMPLE 4

Tablet Formulation

|  | mg/tablet | |
| --- | --- | --- |
|  | 10 mg | 20 mg |
| 7-Methylthio-5-oxo-5H-thiazolo-[2,3-b]quinazoline-2-carboxylic acid | 10.0 | 20.0 |
| Lactose | 182.0 | 172.0 |
| Microcrystalline Cellulose | 60.0 | 60.0 |
| Modified Starch | 15.0 | 15.0 |
| Cornstarch | 30.0 | 0.0 |
| Magnesium Stearate | 3.0 | 3.0 |
| Total | 300 mg. | 300 mg. |

Procedure:

Mix 7-methylthio-5-oxo-5H-thiazolo[2,3-b]quinazoline-2-carboxylic acid, lactose, microcrystalline cellulose, modified starch and cornstarch in a suitable mixer. Then, add magnesium stearate and mix for 5 minutes. Compress on a suitable press.

EXAMPLE 5

Wet Granulation Tablet Formulation

|  | mg/tablet | |
| --- | --- | --- |
|  | 10 mg | 20 mg |
| 7-Methylthio-5-oxo-5H-thiazolo-[2,3-b]quinazoline-2-carboxylic acid | 10.0 | 20.0 |
| Lactose | 264.0 | 254.0 |
| Pregelatinized Starch | 17.5 | 17.5 |
| Cornstarch | 35.0 | 35.0 |
| Modified Starch | 17.5 | 17.5 |
| Magnesium Stearate | 6.0 | 6.0 |
| Total | 350 mg. | 350 mg. |

Procedure:

Mix 7-methylthio-5-oxo-5H-thiazolo[2,3-b]quinazoline-2-carboxylic acid, lactose and pregelatinized starch in a suitable mixer. Mill through suitable mill. Mix with modified starch and magnesium stearate and fill on capsule machine.

I claim:

1. A compound of the formula, 7-methylthio-5-oxo-5H-thiazolo[2,3-b]quinazoline-2-carboxylic acid, 7-methylsulfinyl-5-oxo-5H-thiazolo[2,3-b]quinazoline-2-carboxylic acid or a salt thereof with a pharmaceutically acceptable base.

2. A compound in accordance with claim 1, 7-methylthio-5-oxo-5H-thiazolo[2,3-b]quinazoline-2-carboxylic acid.

3. A compound in accordance with claim 1, 7-methylsulfinyl-5-oxo-5H-thiazolo[2,3-b]quinazoline-2-carboxylic acid.

* * * * *